(12) United States Patent
Harada et al.

(10) Patent No.: US 11,970,442 B2
(45) Date of Patent: Apr. 30, 2024

(54) METHOD FOR PRODUCING CARBONIC ESTER

(71) Applicant: MITSUBISHI GAS CHEMICAL COMPANY, INC., Tokyo (JP)

(72) Inventors: Hidefumi Harada, Tokyo (JP); Takehiko Isobe, Tokyo (JP); Hongyu Liu, Tokyo (JP); Yousuke Shinkai, Tokyo (JP); Ryotaro Umezu, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 938 days.

(21) Appl. No.: 16/960,186

(22) PCT Filed: Jan. 8, 2019

(86) PCT No.: PCT/JP2019/000181
§ 371 (c)(1),
(2) Date: Jul. 6, 2020

(87) PCT Pub. No.: WO2019/138993
PCT Pub. Date: Jul. 18, 2019

(65) Prior Publication Data
US 2021/0061749 A1 Mar. 4, 2021

(30) Foreign Application Priority Data
Jan. 10, 2018 (JP) .................. 2018-001936

(51) Int. Cl.
*C07C 68/04* (2006.01)
(52) U.S. Cl.
CPC .................. *C07C 68/04* (2013.01)

(58) Field of Classification Search
CPC ........ C07C 68/04; C07C 69/96; Y02P 20/141
(Continued)

(56) References Cited

U.S. PATENT DOCUMENTS

2005/0080274 A1 4/2005 Miyake et al.
2019/0185408 A1* 6/2019 Shinkai ................ C07D 213/84

FOREIGN PATENT DOCUMENTS

CN 106336358 A 1/2017
EP 1460056 A1 * 9/2004
(Continued)

OTHER PUBLICATIONS

International Search Report issued in International Patent Application No. PCT/JP2019/000181, dated Apr. 2, 2019 and English Translation thereof.
(Continued)

*Primary Examiner* — Taylor V Oh
(74) *Attorney, Agent, or Firm* — GREENBLUM & BERNSTEIN, P.L.C.

(57) ABSTRACT

To achieve a method for producing a carbonic ester at a high yield by a simple process while suppressing formation of by-products, for example, a method for producing an aliphatic carbonic ester. The above problem is solved by a method for producing a carbonic ester, the method including a carbonic ester formation reaction in which an alcohol and carbon dioxide are reacted in the presence of an aromatic nitrile compound and a catalyst, wherein the water content in the alcohol used in the carbonic ester formation reaction is 0.10% by mass or less.

13 Claims, 13 Drawing Sheets

(58) Field of Classification Search
USPC .......................................................... 558/260
See application file for complete search history.

(56) References Cited

FOREIGN PATENT DOCUMENTS

| | | | |
|---|---|---|---|
| JP | 2006-219483 A | | 8/2006 |
| JP | 2010 77113 A | | 4/2010 |
| JP | 2012 162523 A | | 8/2012 |
| JP | 2012162523 A | * | 8/2012 |
| JP | 2017 160132 A | | 9/2017 |
| WO | 03 055840 A1 | | 7/2003 |
| WO | 2017 221908 A1 | | 12/2017 |

OTHER PUBLICATIONS

Office Action issued to the corresponding Chinese Patent Application No. 201980007418.6 dated Aug. 9, 2022, along with English translation thereof.

* cited by examiner

Reaction conditions

$CeO_2$ : 2.8mmol, 2-CP : 140 mmol, 1-PrOH : 280mmol

Reaction Pressure : 8 MPa,

Reaction temperature : 132°C,

Reaction time : 1~4h

Reaction conditions

CeO$_2$ : 2.8mmol,  2-CP : 140 mmol,  1-PrOH : 280mmol

Reaction Pressure : 8 MPa,

Reaction temperature : 132°C,

Reaction time : 1～4h

Reaction conditions

$CeO_2$ : 1.4mmol, 2-CP : 140 mmol, 1-PrOH : 280~840mmol

Reaction Pressure : 8 MPa,

Reaction temperature : 132°C,

Reaction time : 4h

Reaction conditions

CeO$_2$ : 1.4mmol, 2-CP : 140 mmol, 1-PrOH : 280~840mmol

Reaction Pressure : 8 MPa,

Reaction temperature : 132°C,

Reaction time : 4h

Reaction conditions

CeO$_2$ : 1.4mmol, 2-CP : 140 mmol, 1-PrOH : 840mmol

Reaction Pressure : 8 MPa,

Reaction temperature : 132~147°C,

Reaction time : 2h

Reaction conditions

CeO$_2$ : 1.4mmol, 2-CP : 140 mmol, 1-PrOH : 840mmol

Reaction Pressure : 8 MPa,

Reaction temperature : 132~147°C,

Reaction time : 2h

Reaction conditions

$CeO_2$ : 1.4mmol,  2-CP : 140 mmol,  1-PrOH : 840mmol

Reaction Pressure : 0.6~8 MPa,

Reaction temperature : 132°C,

Reaction time : 1~4h

Reaction conditions

CeO$_2$ : 1.4mmol,  2-CP : 140 mmol,  1-PrOH : 840mmol

Reaction Pressure : 0.6~8 MPa,

Reaction temperature : 132°C,

Reaction time : 1~4h

Reaction conditions

Reaction time : 1~4h, Reaction temperature : 132°C,

1) Reaction Pressure : 0.6~8 MPa $CeO_2$:1.4mmol, 2-CP:140 mmol, 1-PrOH:840mmol

2) Reaction Pressure : 0.5MPa* and 8MPa*

$CeO_2$:2.8mmol, 2-CP:140 mmol, 1-PrOH:280mmol

3) Reaction Pressure : 8MPa'

$CeO_2$:1.4mmol, 2-CP:140 mmol, 1-PrOH:280mmol

Reaction conditions

Reaction time : 1~4h, Reaction temperature : 132°C,

1) Reaction Pressure : 0.6~8 MPa $CeO_2$ : 1.4mmol, 2-CP : 140 mmol, 1-PrOH : 840mmol 2) Reaction Pressure : 0.5MPa* and 8MPa*

$CeO_2$ : 2.8mmol, 2-CP : 140 mmol, 1-PrOH : 280mmol

3) Reaction Pressure : 8MPa'

$CeO_2$ : 1.4mmol, 2-CP : 140 mmol, 1-PrOH : 280mmol

Reaction conditions

$CeO_2$ : 1.4mmol,   2-CP : 140 mmol,   1-PrOH : 840mmol
Reaction Pressure : 8 MPa,
Reaction temperature : 132°C,
Reaction time : 0~1.5h

METHOD FOR PRODUCING CARBONIC ESTER

TECHNICAL FIELD

The present invention relates to a method for producing a carbonate ester such as an aliphatic carbonate ester or the like.

BACKGROUND ART

"Carbonate ester" is a generic name of a compound obtained as a result of one atom or two atoms among two hydrogen atoms of carbonic acid, $CO(OH)_2$, being substituted with an alkyl group or an aryl group, and has a structure of RO—C(=O)—OR' (R and R' each represent a saturated hydrocarbon group or an unsaturated hydrocarbon group).

A carbonate ester is used as an additive such as a gasoline additive for improving the octane value, a diesel fuel additive for decreasing the amount of particles in exhaust gas, or the like. A carbonate ester is also used as, for example, an alkylation agent, a carbonylation agent, a solvent or the like for synthesizing resins or organic compounds such as polycarbonate, urethane, pharmaceutical drugs, agricultural chemicals or the like, a material of an electrolytic solution of lithium ion cells, a material of lubricant oil, or a material of an oxygen absorber for rust inhibition of boiler pipes. As can be seen, a carbonate ester is a very useful compound.

According to a known method for producing a carbonate ester, a carbonate ester is directly synthesized from an alcohol and carbon dioxide using a heterogeneous catalyst. In order to improve the generation amount of the carbonate ester by this method, it has been studied to use an aromatic nitrile compound such as 2-cyanopyridine, benzonitrile or the like as a hydration agent to significantly improve the generation amount and the generation speed of the carbonate ester, to advance the reaction more easily at a pressure close to the normal pressure, and to increase the reaction speed (see Patent Documents 1 and 2). However, there is a problem that such a method does not achieve a satisfactory level of generation amount or generation speed.

CITATION LIST

Patent Literature

Patent Document 1: Japanese Laid-Open Patent Publication No. 2010-77113
Patent Document 2: Japanese Laid-Open Patent Publication No. 2012-162523

SUMMARY OF INVENTION

Technical Problem

In light of the above-described technological problem of the conventional art, an object of the present invention is to realize a method for producing a carbonate ester, for example, an aliphatic carbonate ester, at a high yield by a simple process while suppressing the generation of a by-product.

Solution to Problem

In order to solve the above-described problem, the present inventors made studies on a method for producing a carbonate ester of reacting an alcohol and carbon dioxide under the presence of an aromatic nitrile compound. As a result of examining reaction conditions, the present inventors have made it possible to selectively produce a carbonate ester at a high yield, which is a target compound, by suppressing the amount of moisture in the alcohol and 2-cyanopyridine as materials usable for a carbonate ester generation reaction and thus suppressing the generation of a by-product.

In addition, according to the present invention, the aromatic nitrile compound may be regenerated by a dehydration reaction of an aromatic amide compound generated as a result of hydration. In this case, the carbonate ester may be produced more efficiently. The gist of the present invention is as follows.

[1] A method for producing a carbonate ester, the method comprising a carbonate ester generation reaction of reacting an alcohol and carbon dioxide with each other under the presence of an aromatic nitrile compound and a catalyst,
    wherein a water content of the alcohol which is used for the carbonate ester generation reaction is 0.10% by mass or less.

[2] The method for producing a carbonate ester according to [1] above, wherein a pressure in the carbonate ester generation reaction is 0.6 MPa or higher.

[3] The method for producing a carbonate ester according to [1] or [2] above, wherein a reaction temperature in the carbonate ester generation reaction is 110° C. or higher and 160° C. or lower.

[4] The method for producing a carbonate ester according to any one of [1] through [3] above, wherein a molar ratio of the aromatic nitrile compound and the alcohol is aromatic nitrile compound:alcohol=1:1 to 1:10.

[5] The method for producing a carbonate ester according to any one of [1] through [4] above, wherein a molar ratio of the catalyst, the aromatic nitrile compound and the alcohol is catalyst:aromatic nitrile compound:alcohol=1:100:200 to 0.5:100:600.

[6] The method for producing a carbonate ester according to any one of [1] through [5] above, wherein the aromatic nitrile compound comprises 2-cyanopyridine.

[7] The method for producing a carbonate ester according to any one of [1] through [6] above, wherein the catalyst contains $CeO_2$.

[8] The method for producing a carbonate ester according to any one of [1] through [7] above, wherein the alcohol comprises an aliphatic alcohol, and at least an aliphatic carbonate ester is generated as the carbonate ester.

[9] The method for producing a carbonate ester according to any one of [1] through [8] above, wherein the aliphatic alcohol is expressed by the following formula (1):

$$R\text{—}OH \tag{1}$$

(in formula (1), R is a straight or branched-chain saturated aliphatic alkyl group that may contain a substituent and has a carbon number of 1 to 10).

[10] The method for producing a carbonate ester according to [9] above, wherein R in formula (1) is a saturated aliphatic alkyl group having a carbon number of 1 to 4.

[11] The method for producing a carbonate ester according to any one of [8] through [10] above, wherein the aliphatic alcohol comprises 1-propanol.

[12] The method for producing a carbonate ester according to any one of [1] through [11] above, further comprising at least one of:
    a first alcohol dehydration step of dehydrating the alcohol before the alcohol is used for the carbonate ester generation reaction; and a second alcohol dehydration step of dehydrating the alcohol after the alcohol is used for the carbonate ester generation reaction in order to reuse the alcohol.

[13] The method for producing a carbonate ester according to any one of [1] through [12] above, further comprising a regeneration step of, after the aromatic nitrile compound is hydrated with water generated by the carbonate ester generation reaction to generate an aromatic amide compound, dehydrating the aromatic amide compound to regenerate the aromatic nitrile compound.

[14] The method for producing a carbonate ester according to any one of [1] through [13] above, further comprising a control step of storing the alcohol while keeping the water content of the alcohol at 0.10% by mass or less.

Advantageous Effects of Invention

According to the present invention described above, the moisture amount in the alcohol to be used to produce the carbonate ester is suppressed, so that the carbonate ester as the target compound may be selectively produced at a high yield while the generation of a by-product is suppressed. Also according to the present invention, the activity of the catalyst may be fully restored so as to make the catalyst reusable. As described below in detail, for example, the type of the alcohol for washing and the type of the alcohol to be used to produce the carbonate ester are adjusted, so that the yield of the carbonate ester may be improved and the process for producing the carbonate ester may be simplified.

As described above, the present invention may realize an efficient method for producing a carbonate ester by which the carbonate ester as the target compound is produced at a high yield while the generation of a by-product is suppressed.

DESCRIPTION OF EMBODIMENTS

Figure 1:
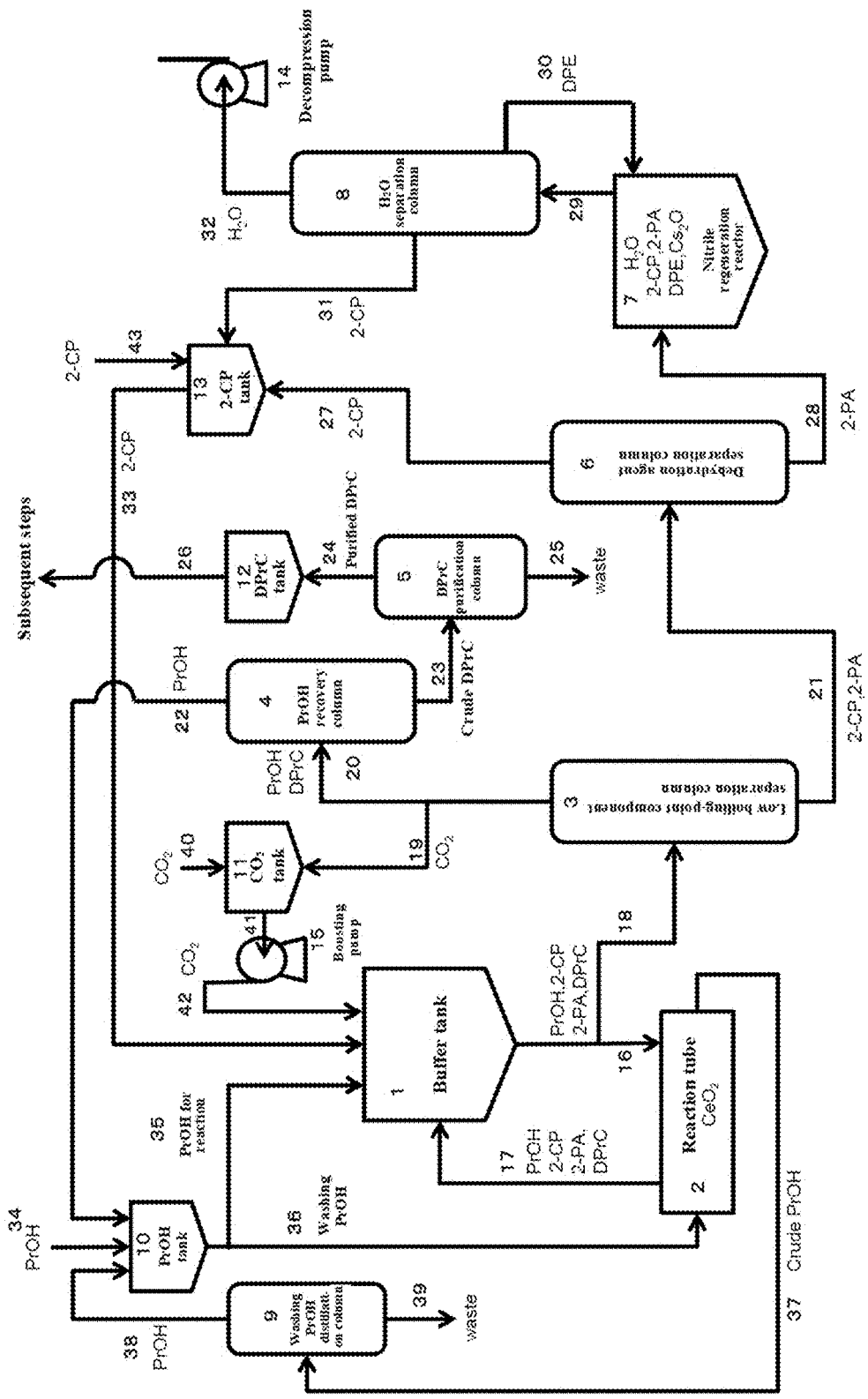
FIG. 1 shows an example of carbonate ester production device.

Hereinafter, a preferred embodiment of the present invention will be described in detail with reference to the attached drawings. In the specification and the drawings, components having substantially the same functions or structures will bear the same reference signs, and the same descriptions will not be repeated.

<1. Method for Producing a Carbonate Ester>

A method according to the present invention for producing a carbonate ester includes a carbonate ester generation reaction of generating a carbonate ester from carbon dioxide and an alcohol. For the carbonate ester generation reaction, an aliphatic alcohol, for example, is used as the alcohol to generate an aliphatic carbonate ester. Hereinafter, such a method for producing a carbonate ester will be described.

(Carbonate Ester Generation Reaction)

The method according to the present invention for producing a carbonate ester includes a step of causing a reaction of directly reacting an alcohol and carbon dioxide with each other under the presence of a solid catalyst containing, for example, $CeO_2$ (cerium oxide) or the like (carbonate ester generation reaction) to obtain a carbonate ester. A specific example of the carbonate ester generation reaction in which propanol (PrOH: e.g., 1-propyl alcohol) is used to obtain dipropyl carbonate (O=C(OPr)$_2$:DPrC) is represented by the following formula (2).

[Chemical formula 1]

$$CO_2 + 2PrOH \rightleftharpoons DPrC + H_2O \qquad (2)$$

(Alcohol in the Carbonate Ester Generation Reaction)

An alcohol usable for the carbonate ester generation reaction is preferably an aliphatic alcohol. As the aliphatic alcohol, any one of primary alcohol, secondary alcohol and tertiary alcohol is usable. Alternatively, the aliphatic alcohol may be a mixture of one, or two or more, of these alcohols. It should be noted that the alcohol usable in the carbonate ester generation reaction is not limited to the aliphatic alcohol.

For example, in the formula (1) presented above, R of R—OH is an aryl group or the like that may encompass a phenyl group, a benzyl group or a plurality of rings (may be condensed rings). R is preferably either one of an aromatic group that may contain a substituent such as halogen or the like, and a straight or branched-chain saturated aliphatic alkyl group that may contain a substituent such as halogen or the like and has a carbon number of 1 to 10. More preferably, the alcohol represented by formula (1) is an aliphatic alcohol as described above. In the case where R is an aliphatic group, the carbon number of R in formula (1) is preferably 1 to 8, more preferably 1 to 6, still more preferably 1 to 4, and especially preferably 2 to 4. In the case where R is an aromatic group, the carbon number of R in formula (1) is preferably 6 to 24, more preferably 6 to 20, and still more preferably 6 to 16.

In the case of being an aliphatic alcohol, R in formula (1) may be either a saturated or unsaturated aliphatic alkyl group. For example, R may include three or less unsaturated bonds, but preferably R is a saturated aliphatic alkyl group. Namely, R in formula (1) is preferably a saturated aliphatic alkyl group having a carbon number of 1 to 8, more preferably a saturated aliphatic alkyl group having a carbon number of 1 to 6, and especially preferably a saturated aliphatic alkyl group having a carbon number of 1 to 4.

Specific examples of such an aliphatic alcohol as a material usable for the carbonate ester generation reaction include methanol, ethanol, 1-propanol, isopropanol (2-propanol), 1-butanol, 2-butanol, isobutylalcohol, tert-butylalcohol, 1-pentanol, 1-hexanol, 1-heptanol, 1-octanol, 1-nonanol, allyl alcohol, 2-methyl-1-propanol, cyclohexanemethanol, ethyleneglycol, 1,2-propanediol, 1,3-propanediol and the like. Use of these alcohols increases the yield of the product and also increases the reaction speed, and therefore is preferred. The carbonate esters generated by use of the above-listed alcohols are respectively dimethyl carbonate, diethyl carbonate, dipropyl carbonate, diisopropyl carbonate, dibutyl carbonate, dipentyl carbonate, dihexyl carbonate, diheptyl carbonate, dioctyl carbonate, dinonane carbonate, diallyl carbonate, di-2-methyl-propyl carbonate, dicyclohexanemethyl carbonate, dibenzyl carbonate, ethylene carbonate, 1,2-propylene carbonate, and 1,3-propylene carbonate.

Among the above-listed specific examples, it is preferred to use propanol or butanol, especially, 1-propanol (n-propylalcohol).

In the case where the carbonate ester obtained by the carbonate ester generation reaction is used as a material of diaryl carbonate, it is preferred to use an alcohol having a carbon number of 1 to 6, and it is more preferred to use an alcohol having a carbon number of 1 to 4, among the above-listed specific examples.

(Amount of Moisture in the Alcohol to be Used for the Carbonate Ester Generation Reaction)

In the carbonate ester generation reaction, an alcohol having an amount of moisture as impurities of 0.10% by mass or less is used as a material. The moisture amount in the alcohol to be used in the carbonate ester generation reaction is preferably 0.09% by mass or less, more preferably 0.08% by mass or less, still more preferably 0.07% by mass or less, for example, 0.064% by mass or less, and especially preferably 0.05% by mass or less.

When the carbonate ester generation reaction is continued for a relatively long time period, the amount of water as an unremovable by-product and the amount of moisture brought by the supplemented material increase, or the material stored in a tank or the like absorbs moisture in the environment. As a result, the amount of water in the material is recognized to tend to be increased little by little. In order to keep the reaction conditions in a good state for a long time period in such a situation, it is preferred to suppress the amount of moisture contained in the alcohol to be used for the carbonate ester generation reaction or in 2-cyanopyridine to be used for the carbonate ester generation reaction as a dehydration agent. Especially, the alcohol is used in a larger amount than the dehydration agent, and is consumed by the reaction and thus needs to be supplemented successively. Therefore, it is desired to control the amount of moisture in the alcohol. The amount of moisture in the alcohol at the start of the reaction is preferably 0.04% by mass or less, more preferably 0.02% by mass or less, still more preferably 0.01% by mass or less, and especially preferably 0.005% by mass or less.

In the case where the moisture amount in the alcohol to be used for the carbonate ester generation reaction exceeds 0.14%, the yield of the carbonate ester, which is the target compound, is decreased, and the amount of a by-product is recognized to tend to be increased. Therefore, it is desired that the moisture amount in the alcohol is 0.14% or less.

(Step of Dehydrating an Alcohol)

It is preferred that an alcohol containing a relatively large amount of moisture is dehydrated before being used for the carbonate ester generation reaction. Therefore, regarding the carbonate ester generation reaction, it is preferred to perform a step of dehydrating pre-use alcohol, which may contain alcohol to be supplemented (first alcohol dehydration step) and also a step of dehydrating the alcohol stored in, for example, a tank or the like to be reused after being used for the carbonate ester generation reaction (second alcohol dehydration step).

These dehydration steps use a drying agent such as, for example, a molecular sieve, calcium oxide, active anhydrous calcium sulfate, magnesium oxide, magnesium sulfate, anhydrous potassium carbonate, silica gel or the like, and a technique such as, for example, fractional distillation in a distillation column. For the second alcohol dehydration step, it is preferred that a dehydration tank or a dehydration line filled with a dehydration agent is provided independently from a reaction system such as, for example, a tank that stores the alcohol, and that the alcohol is circulated in the dehydration tank or the dehydration line to be dehydrated. Reuse of the alcohol having the moisture amount therein decreased in this manner allows the carbonate ester to be generated at a high yield while activating a reaction device continuously for a long time period.

(Step of Controlling the Alcohol)

In order to suppress the moisture amount in the alcohol to be used for the carbonate ester generation reaction with certainty, it is preferred to store the alcohol while measuring the moisture amount therein when necessary. In the case where the alcohol is stored, it is preferred that the storage of the alcohol is performed while the moisture amount therein is controlled so as not to exceed a predetermined reference value, for example, 0.10% by mass. Such a control to keep the moisture amount in the alcohol at 0.10% by mass or less allows alcohol, having the moisture amount therein suppressed to a predetermined level or lower, to be used for the carbonate ester generation reaction.

In the control step, it is preferred that the moisture amount in the alcohol to be used for the carbonate ester generation reaction is kept at 0.09% by mass or less. In the control step, the moisture amount in the alcohol to be used for the carbonate ester generation reaction is kept more preferably at 0.08% by mass or less, still more preferably at 0.07% by mass or less, for example, at 0.064% by mass or less, and especially preferably at 0.05% by mass or less.

(Catalyst Usable for Producing the Carbonate Ester)

For the carbonate ester generation reaction, it is preferred that a catalyst containing $CeO_2$ as an activation component is used. A catalyst containing $ZrO_2$, $ReO_2$, NiO, $Al_2O_3$, $Y_2O_3$ or the like as a component other than $CeO_2$ is usable. A preferred catalyst usable for the carbonate ester generation reaction is a solid catalyst containing, for example, only $CeO_2$, a mixture of $CeO_2$ and $ZrO_2$, a solid solution of $CeO_2$ and $ZrO_2$, or a composite oxide of $CeO_2$ and $ZrO_2$, or the like. It is especially preferred to use a solid catalyst containing only $CeO_2$ as an activation component. The mixing ratio of $CeO_2$ and $ZrO_2$ in the solid solution or the composite oxide of $CeO_2$ and $ZrO_2$ is basically 50:50, but may be changed appropriately.

The catalyst usable for the carbonate ester generation reaction may be either in the form of powder or in the form of a molded body. In consideration of the activity, it is preferred that the catalyst is powder. By contrast, in consideration of the infiltration step and the separation step, it is preferred that the catalyst is a molded body. In the case of being a molded body, the catalyst may be either spherical, pellet-like, cylindrical, ring-shaped, wheel-shaped, granular or the like.

A catalyst containing $CeO_2$ or the like as an activation component carried by a carrier may be used. For example, a catalyst containing an activation component carried by one or two among $SiO_2$, $ZrO_2$, $Al_2O_3$, $TiO_2$, activated carbon, zeolite and the like as a carrier may be used.

The catalyst has an average particle diameter of preferably 0.01 to 200 μm, more preferably 1 to 100 μm, and especially preferably 5 to 50 μm. The catalyst has a specific surface area of preferably 50 to 200 $m^2/g$, more preferably 70 to 200 $m^2/g$, and especially preferably 100 to 200 $m^2/g$.

The above-mentioned numerical value ranges of the average particle diameter and the specific surface area are for particles substantially containing only an activation component such as $CeO_2$ or the like, for example, particles containing an activation component at a content of 99% by weight or more. In the case where the catalyst includes a carrier or a molded body, the above-mentioned numerical value ranges of the average particle diameter and the specific surface area are not for particles including the carrier or the molded body. In the case where the catalyst contains a carrier or a molded body, it is preferred that particles of an activation component to be used to produce the catalyst has an average particle diameter and a specific surface area in the above-described numerical value ranges.

In the case where the catalyst contains a component other than the activation component, for example, a component such as a carrier or a molded body, the catalyst contains an activation component at a content of preferably at least 50% by weight, more preferably at least 70% by weight, and especially preferably at least 90% by weight.

(Carbon Dioxide)

Carbon dioxide to be used for the carbonate ester generation reaction is not limited to carbon dioxide prepared as industrial gas, but encompasses carbon dioxide separated and recovered from exhaust gas of plants producing various products, steel manufacturing plants, electric power plants or the like.

(Aromatic Nitrile Compound)

Examples of the aromatic nitrile compound to be used for the carbonate ester generation reaction include 2-cyanopyridine (2-CP), cyanopyrazine, benzonitrile and the like. Among these substances, 2-cyanopyridine is especially preferred.

(Use of a Solvent in the Carbonate Ester Generation Reaction)

In the carbonate ester generation reaction, the catalyst is powdery. Therefore, the catalyst and the reaction system may be easily separated from each other by an operation such as infiltration or the like. This makes it unnecessary to perform solid-liquid separation by distillation. For this reason, it is not necessary to use a solvent. Since neither the carbonate ester generation reaction nor the method for producing a carbonate ester including the carbonate ester generation reaction uses a solvent as described above, the number of types of components required in the reaction system may be minimized. It should be noted that a solvent may be used for the carbonate ester generation reaction. An example of solvent usable for the carbonate ester generation reaction is either one of dialkylbenzene, alkylnaphthalene, diphenylbenzene and the like.

(Hydration Step)

When an alcohol and carbon dioxide are reacted with each other in the carbonate ester generation reaction as shown in formula (2), water is generated in addition to the carbonate ester. Therefore, it is preferred to remove water from the reaction system in order to efficiently generate the carbonate ester by the equilibrium reaction shown in formula (2). For this purpose, it is preferred to incorporate a nitrile compound, preferably, an aromatic nitrile compound, into the reaction system to generate an amide compound by a hydration reaction of the nitrile compound with water and to remove the generated water from the reaction system.

As described above, a hydration step of hydrating the aromatic nitrile compound with water, which is a by-product, to generate an aromatic amide compound may be used. In this case, water is efficiently removed from the reaction system, and thus the generation of the carbonate ester may be promoted. This is expressed by, for example, the following formula (3).

[Chemical formula 2]

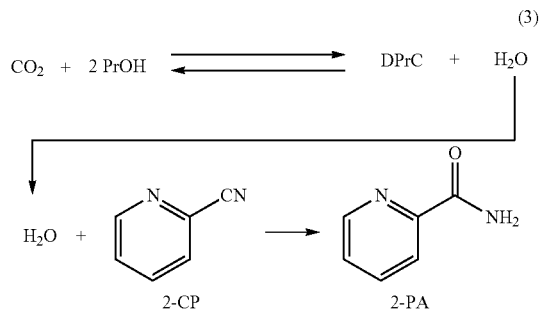

(3)

(Step of Regenerating the Aromatic Nitrile Compound)

As shown in formula (3) above, the aromatic amide compound is generated as a by-product as a result of the hydration step. Preferably, the aromatic amide compound thus generated as a by-product is separated from the system after the carbonate ester generation reaction, and then is dehydrated, to regenerate the aromatic nitrile compound. The regenerated aromatic nitrile compound is reusable for the above-described hydration step.

An example of method for generating (regenerating) the aromatic nitrile compound as described above uses a reaction, expressed by the following formula (4), which is caused in the presence of a catalyst containing a basic metal oxide such as $Cs_2O$ or the like and a predetermined solvent.

In this reaction, 2-picolinamide, which is an aromatic amide compound, is converted into 2-cyanopyridine, which is an aromatic nitrile compound, by a dehydration reaction.

[Chemical formula 3]

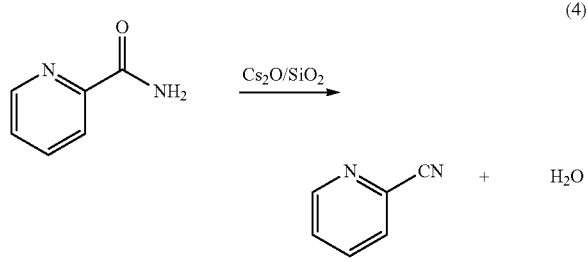

(4)

The catalyst usable in the dehydration reaction according to the present invention contains an oxide of an alkaline metal (K, Li, Na, Rb, Cs), which is to become basic. For the above-described reaction, it is especially preferred to use a catalyst containing an oxide of at least one of Na, K, Rb and Cs (cesium). As a carrier for the catalyst, a substance that is commonly used as a carrier is usable. As a result of examining various carriers, it has been found out that a catalyst carried by one or two among $SiO_2$ and $ZrO_2$ is preferably usable.

When the above-described carbonate ester generation reaction is continued, the activity of the catalyst is decreased. Therefore, a used catalyst may be regenerated after being separated and recovered. A method for regenerating the catalyst includes, for example, a step of separating a catalyst, that has been used for a certain time period, as a crude catalyst from a reaction system and washing the catalyst with a washing solution such as a washing alcohol or the like, and a baking step. A preferred washing alcohol is of the same type as the alcohol to be used for the carbonate ester generation reaction.

(Pressure in the Carbonate Ester Generation Reaction)

A preferred reaction pressure for generating a carbonate ester is 0.6 MPa (absolute pressure) or higher. In the case where the reaction pressure is 0.6 MPa (absolute pressure) or higher, the carbonate ester as the target compound may be obtained at a high yield and the generation of a by-product may be suppressed. By contrast, in the case where the reaction pressure is set to be low, a decompression device is required, which makes the facilities complicated and increases the cost. In addition, in such a case, a motive power energy is required to decrease the pressure, which decreases the energy efficiency.

The upper limit of the reaction pressure may be set to, for example, about 20 MPa (absolute pressure). The reaction pressure is preferably 10 MPa or lower, and more preferably 8 MPa or lower. In the case where the reaction pressure is too high, the hydration reaction with the aromatic nitrile compound is difficult to advance, which may possibly decrease the yield of the carbonate ester. In addition, in such a case, a motive power energy is required to increase the pressure, which decreases the energy efficiency.

For the above reasons, the pressure in the carbonate ester generation reaction is preferably in the range of 0.6 to 8 MPa (absolute pressure), more preferably in the range of 1.0 to 6.0 MPa, and still more preferably in the range of 2.0 to 4.0 MPa.

(Reaction Temperature for Generating the Carbonate Ester)

The reaction temperature (temperature of the reaction solution) in the carbonate ester generation reaction may be adjusted in the range of about 50 to about 300° C. The reaction temperature is preferably 110° C. or higher and 160° C. or lower. In the case where the reaction temperature is too low, the reaction speed is low, and therefore, the carbonate ester synthesis reaction and the hydration reaction with the aromatic nitrile compound are both difficult to advance, which tends to decrease the productivity of the carbonate ester. In the case where the reaction temperature is too high, the reaction speed of each of the above-described reactions is high, but the carbonate ester is easily decomposed and denatured, and also, for example, a side reaction of 2-picolinamide and an alcohol is easily caused, which tend to decrease the yield of the carbonate ester. The reaction temperature is more preferably 100 to 150° C.

For the above-described reasons, the temperature in the carbonate ester generation reaction is preferably in the range of 110° C. or higher and 160° C. or lower, more preferably in the range of 120° C. or higher and 155° C. or lower, still more preferably 125° C. or higher and 150° C. or lower, and especially preferably 130° C. or higher and 145° C. or lower.

An ideal reaction temperature is considered to vary in accordance with the type or the amount of the solid catalyst or the amount or the ratio of the materials (alcohol and aromatic nitrile compound). Therefore, it is desired to set the optimal conditions in each case. Since the preferred reaction temperature is 110° C. to 160° C., it is desired to pre-heat the materials (alcohol and aromatic nitrile compound) with steam or the like before the materials are used for the carbonate ester generation reaction.

(Ratio of Components in the Carbonate Ester Generation Reaction)

In the carbonate ester generation reaction, the molar ratio of the aromatic nitrile compound and the alcohol is preferably aromatic nitrile compound:alcohol=1:1 to 1:10. The ratio (molar ratio) of the aromatic nitrile compound and the alcohol is more preferably 1:1 to 1:8, and especially preferably 1:2 to 1:6.

The molar ratio of the catalyst, the aromatic nitrile compound and the alcohol is preferably catalyst:aromatic nitrile compound:alcohol=1:100:200 to 0.5:100:600. The ratio (molar ratio) of the catalyst, the aromatic nitrile compound and the alcohol is more preferably catalyst:aromatic nitrile compound:alcohol=0.9:100:300 to 0.6:100:500, and especially preferably catalyst:aromatic nitrile compound:alcohol=0.8:100:400 to 0.7:100:500.

The molar ratio of the catalyst and the aromatic nitrile compound is preferably catalyst:aromatic nitrile compound=10 to 0.05:100, and more preferably 1 to 0.5:100. The molar ratio of the catalyst and the alcohol is preferably catalyst:alcohol=1:10 to 1:1200, and more preferably 1:200 to 1:1200. In the case where the ratio of the components in the carbonate ester generation reaction is adjusted in the above-described range, the yield of the carbonate ester may be increased and the generation of a by-product may be suppressed.

<2. Carbonate Ester Production Device>

Figure 2:
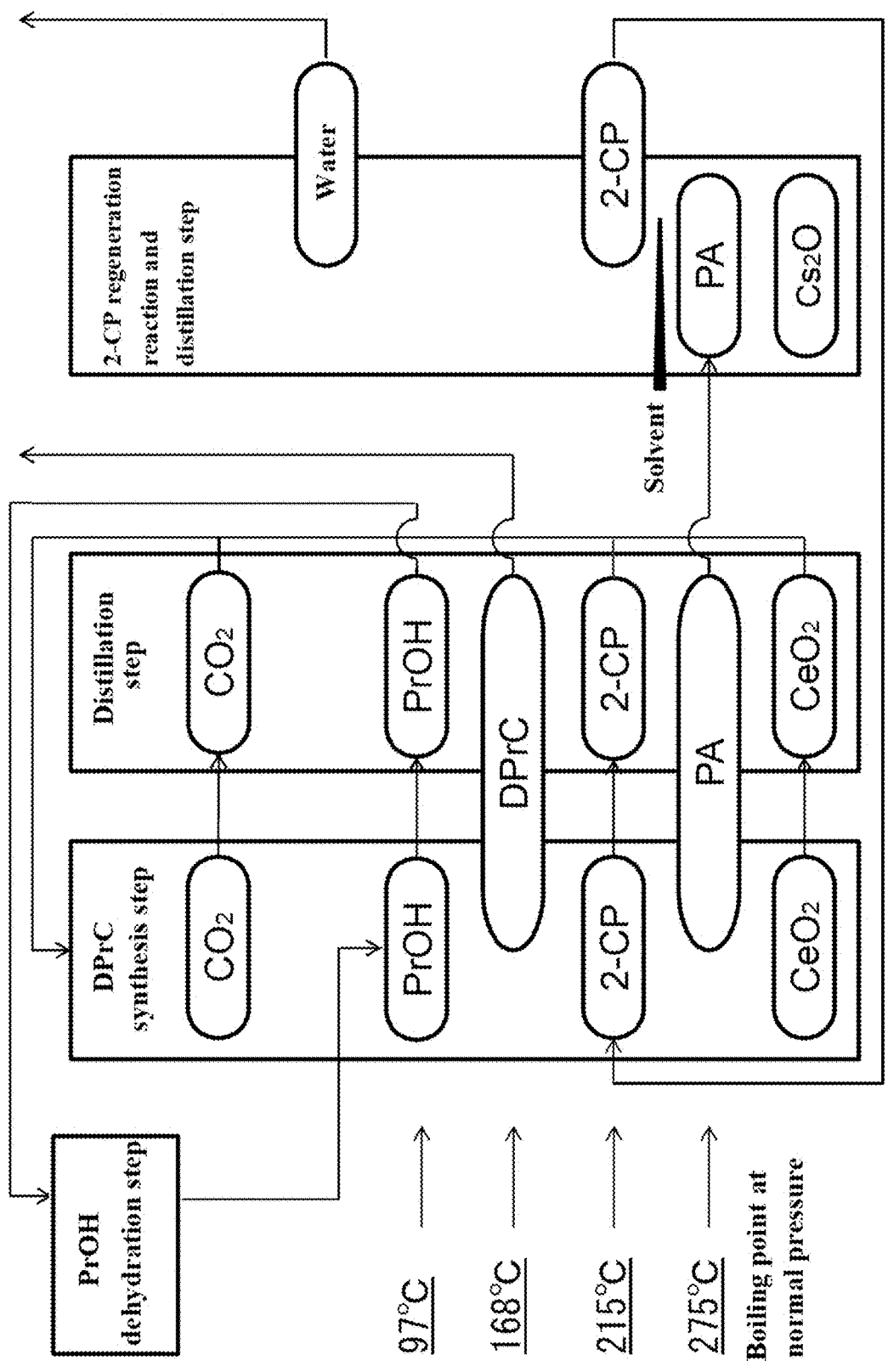
FIG. 2 is a chart showing the state of each of substances in each of steps performed by use of the production device shown in FIG. 1.
Figure 3:
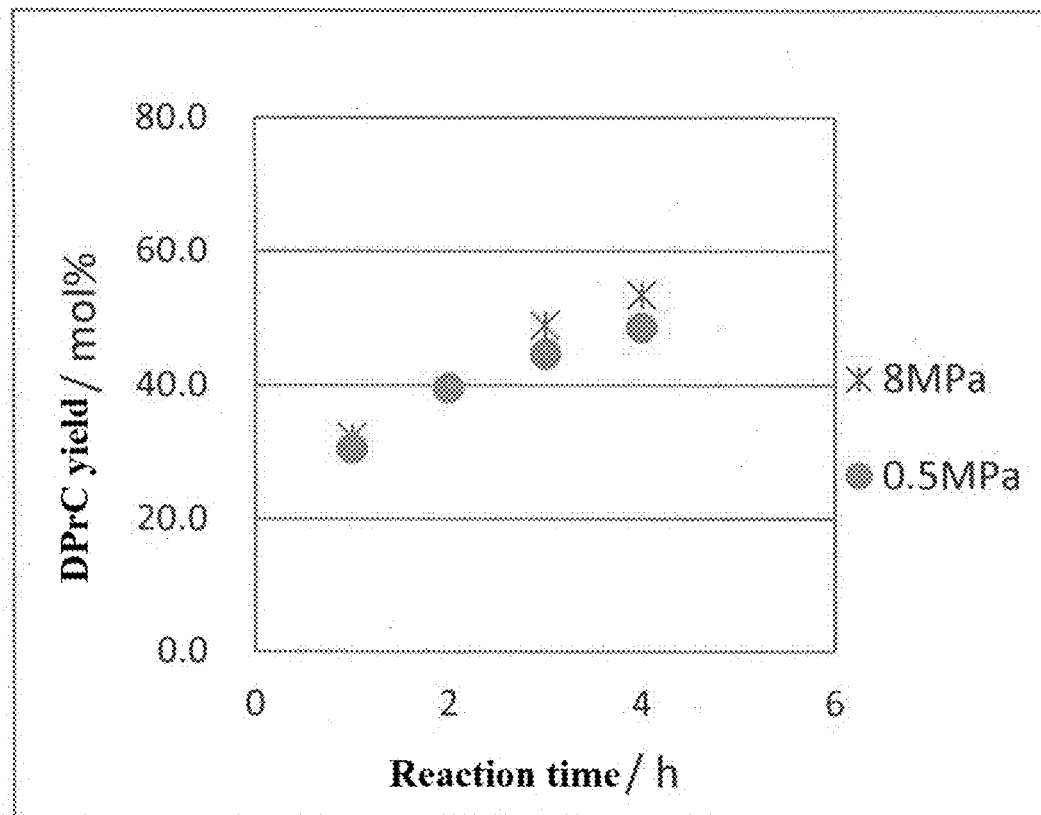
FIG. 3 is a graph showing the yield of the carbonate ester in a carbonate ester generation reaction performed while the reaction pressure is varied.
Figure 4:
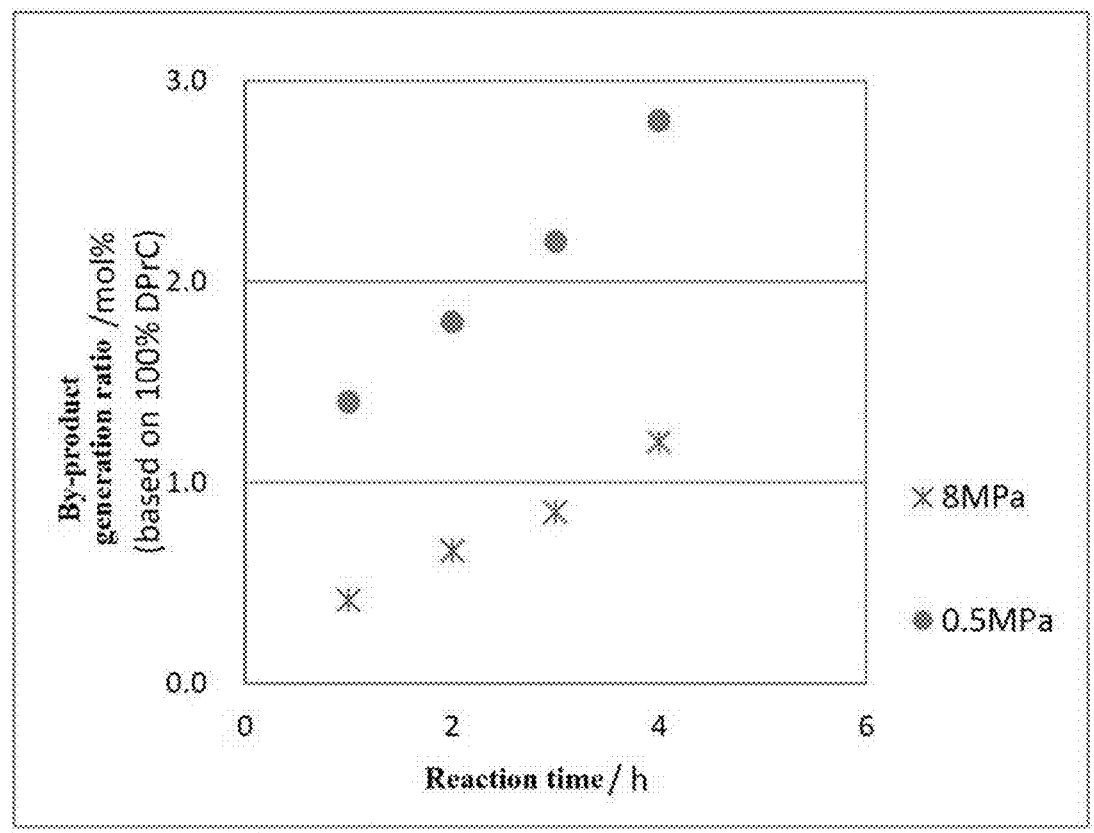
FIG. 4 is a graph showing the generation ratio of the by-products in the carbonate ester generation reaction performed while the reaction pressure is varied.
Figure 5:
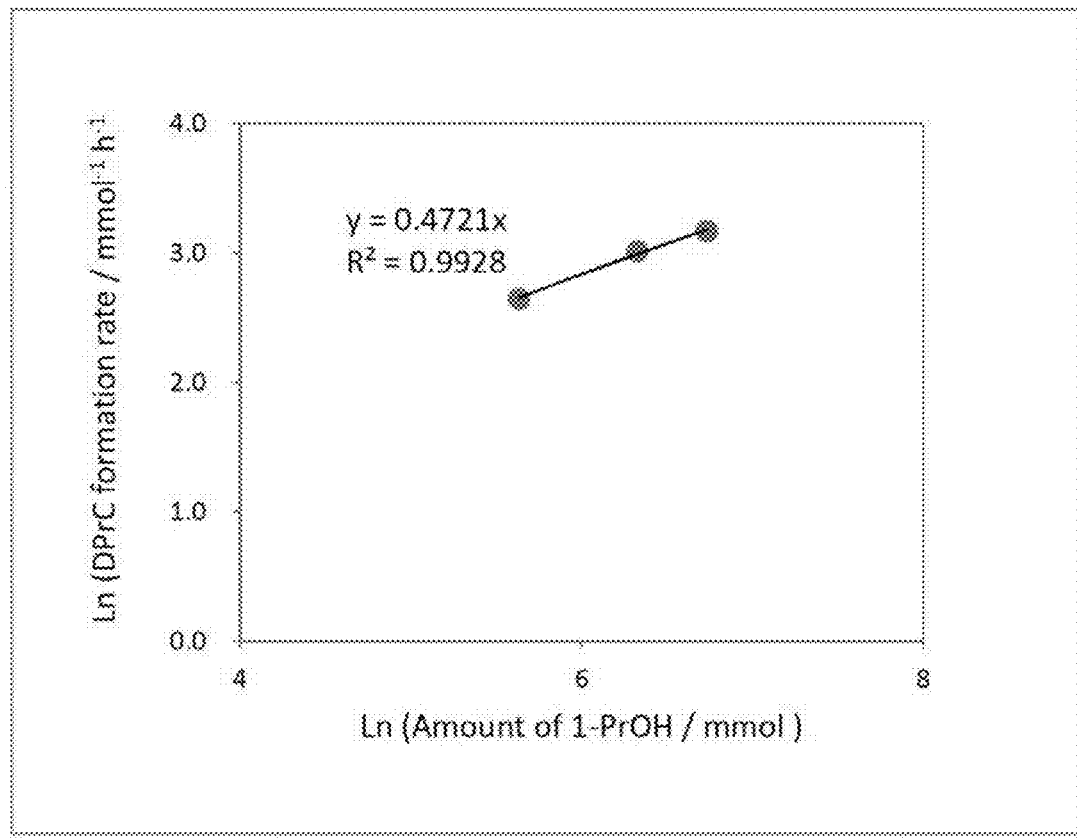
FIG. 5 is a graph showing the yield of the carbonate ester in a carbonate ester generation reaction performed while the ratio of the alcohol and the aromatic nitrile compound as materials is varied.
Figure 6:
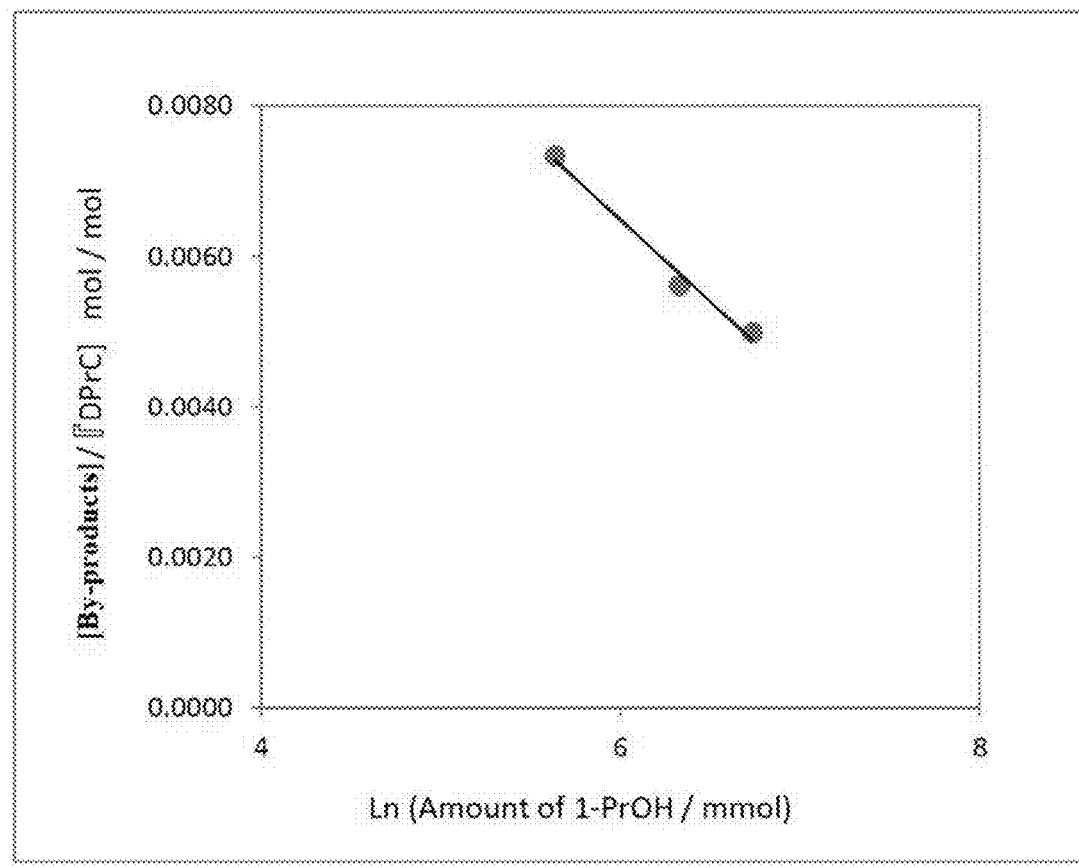
FIG. 6 is a graph showing the generation ratio of the by-products in the carbonate ester generation reaction performed while the ratio of the alcohol and the aromatic nitrile compound as materials is varied.
Figure 7:
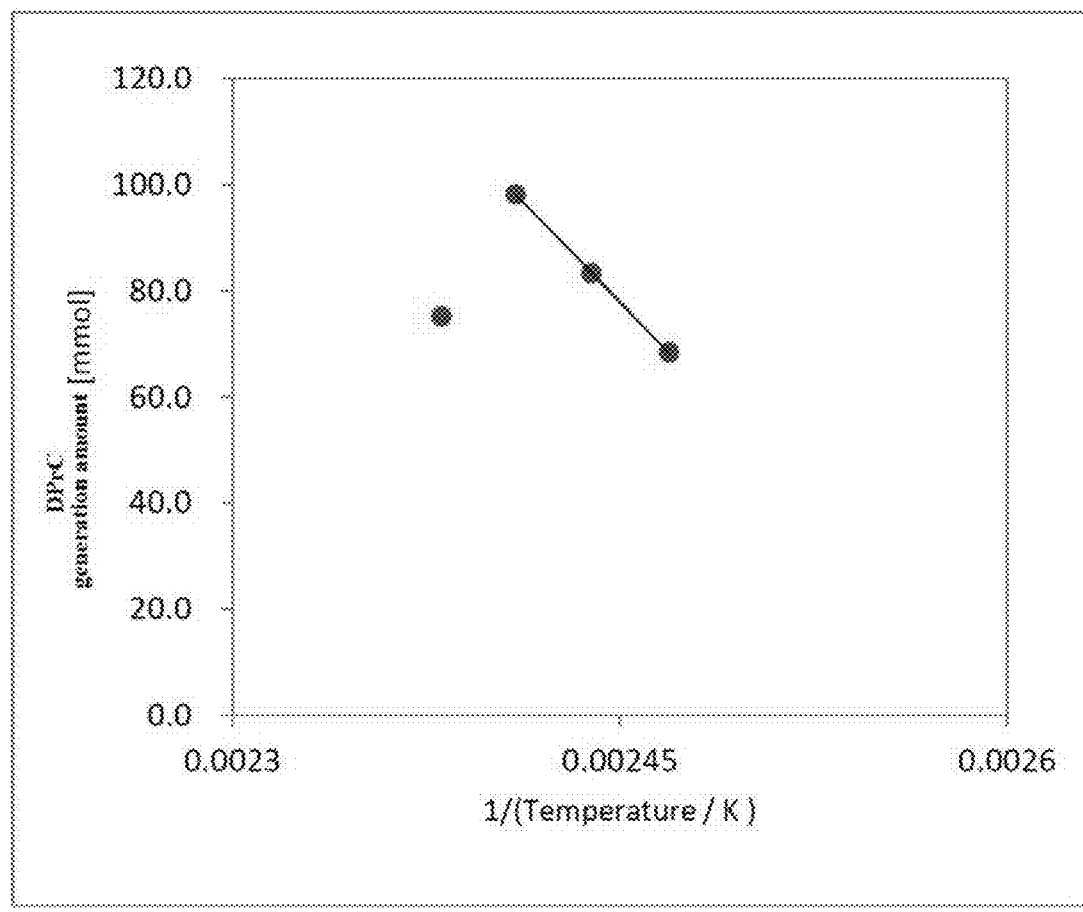
FIG. 7 is a graph showing the yield of the carbonate ester in a carbonate ester generation reaction performed while the reaction temperature is varied.
Figure 8:
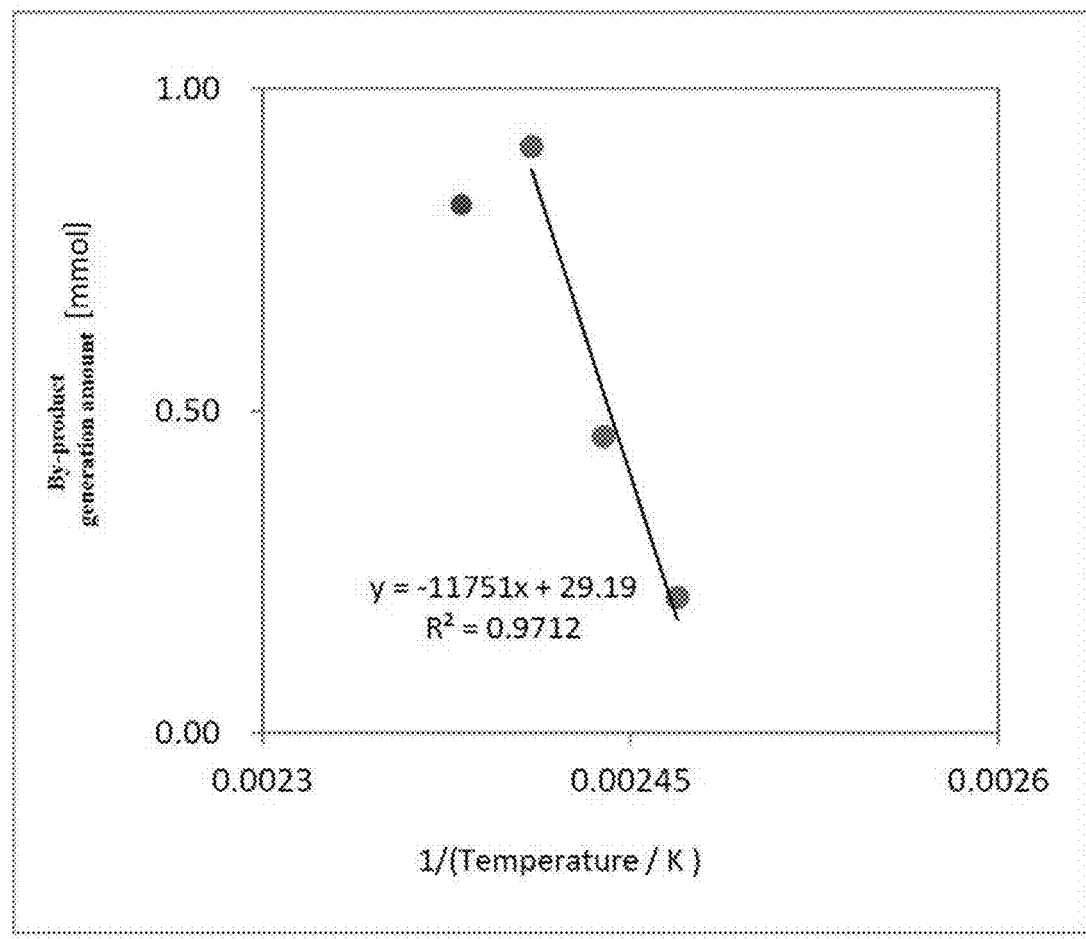
FIG. 8 is a graph showing the generation amount of the by-products in the carbonate ester generation reaction performed while the reaction temperature is varied.
Figure 9:
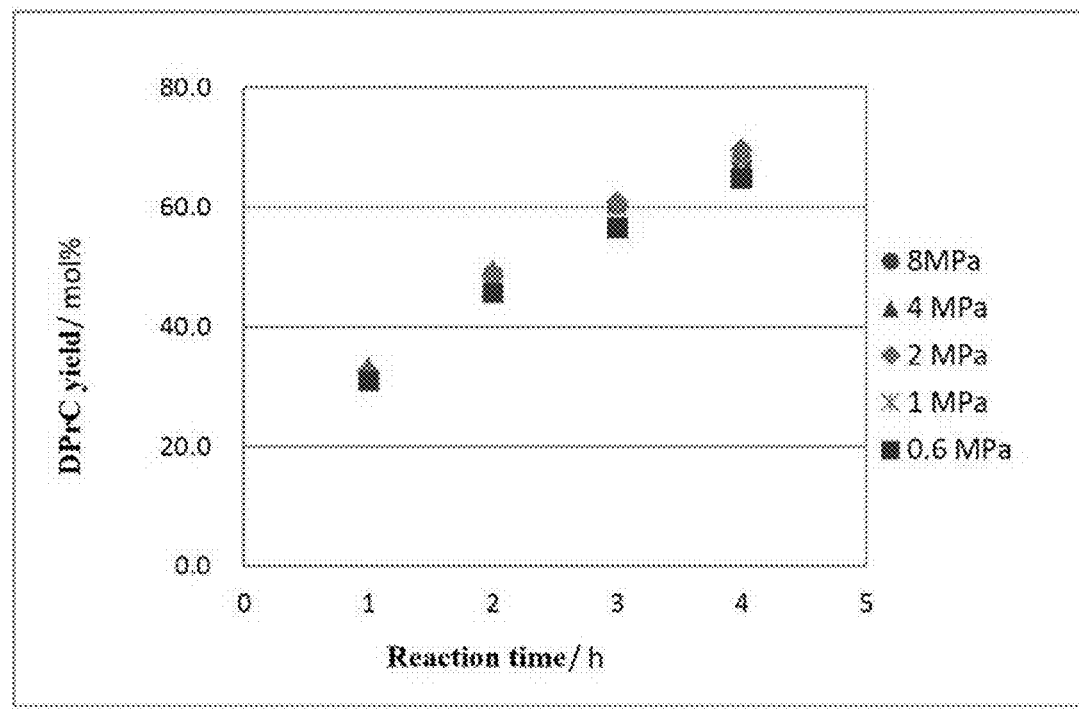
FIG. 9 is a graph showing the yield of the carbonate ester in a carbonate ester generation reaction performed while the reaction pressure is varied under the reaction conditions in which the ratio of the aromatic nitrile compound with respect to the alcohol is different from that in the reaction, the results of which are shown in FIG. 3.
Figure 10:
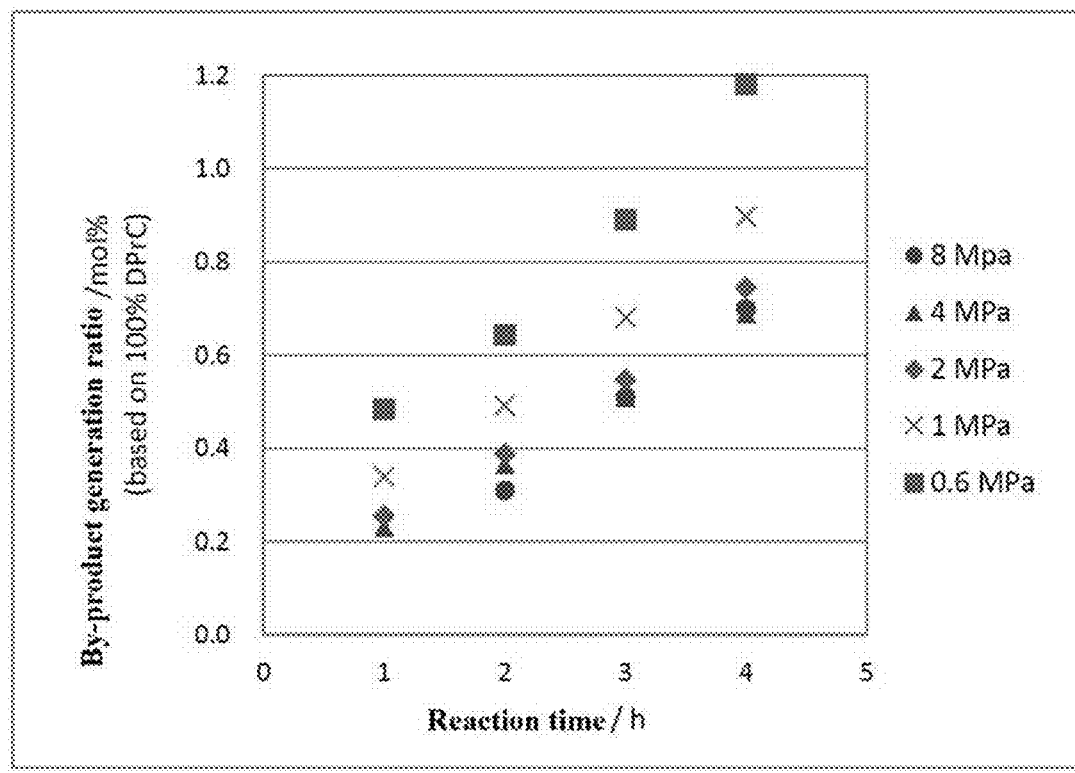
FIG. 10 is a graph showing the generation ratio of the by-products in the carbonate ester generation reaction performed while the reaction pressure is varied under the reaction conditions in which the ratio of the aromatic nitrile compound with respect to the alcohol is different from that in the reaction, the results of which are shown in FIG. 3.
Figure 11:
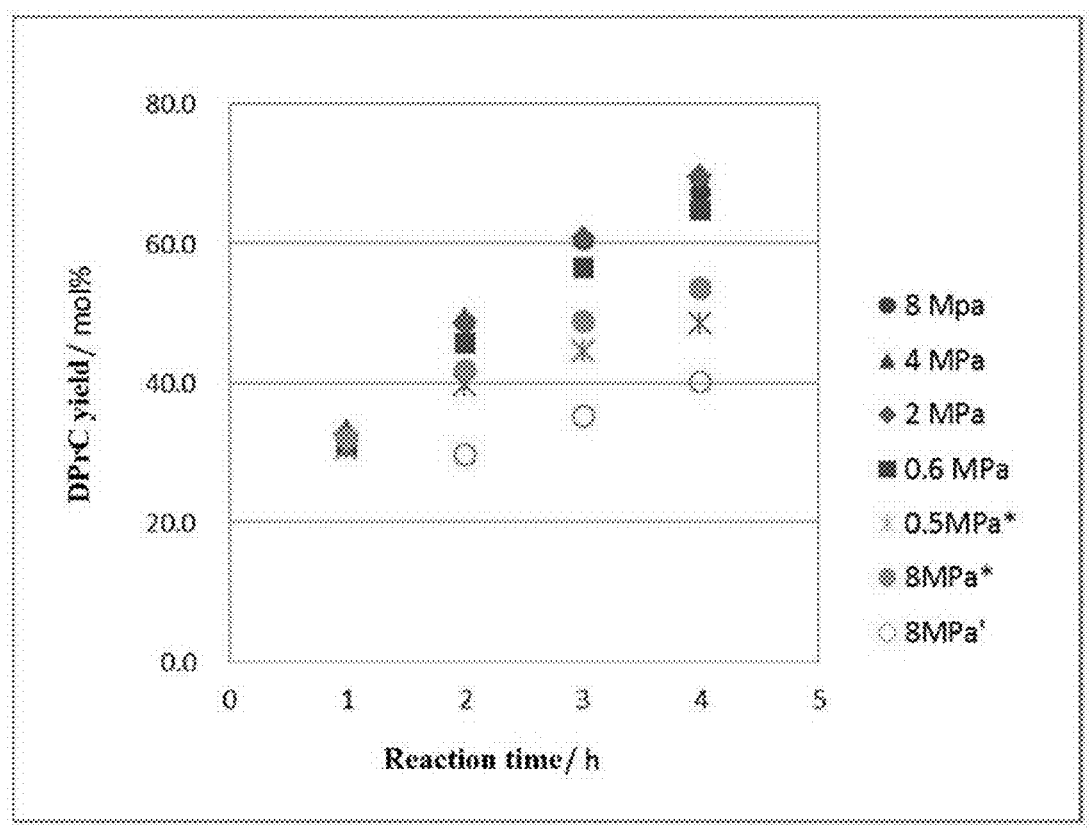
FIG. 11 is a graph showing the yield of the carbonate ester in a carbonate ester generation reaction performed while the reaction pressure is varied under the reaction conditions in which the amount of the catalyst is different from that in the reaction, the results of which are shown in FIG. 9.
Figure 12:
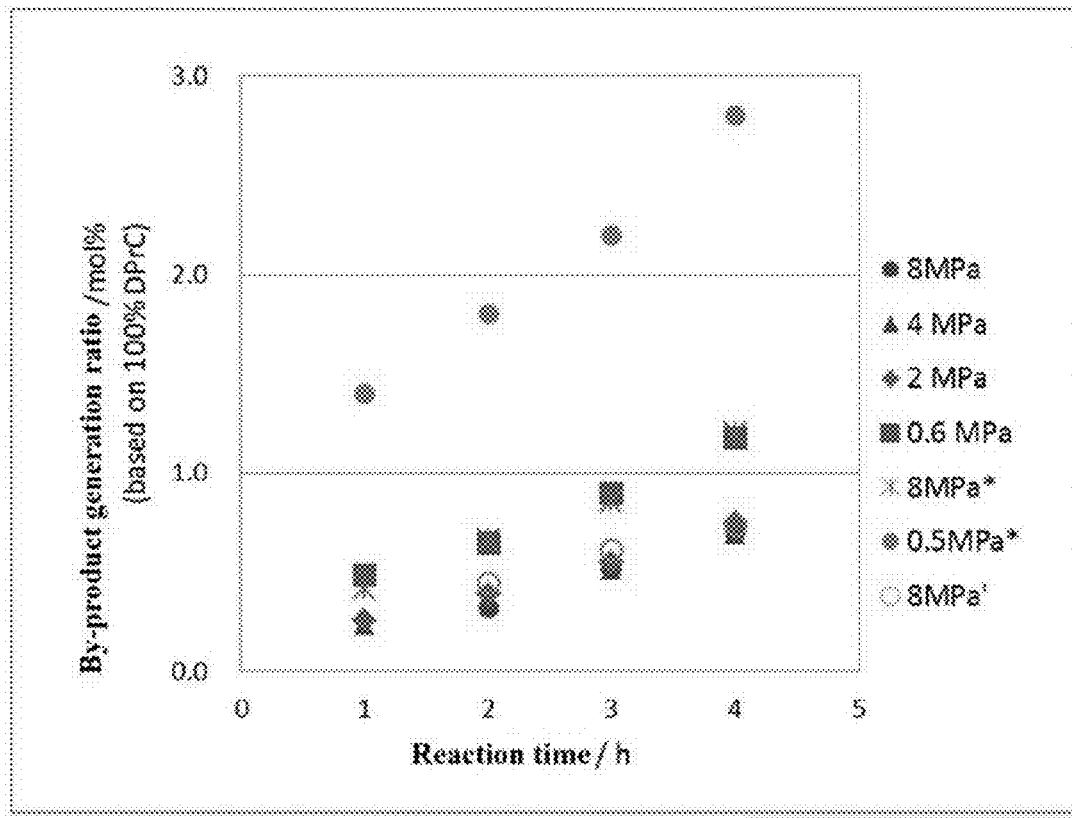
FIG. 12 is a graph showing the generation ratio of the by-products in the carbonate ester generation reaction performed while the reaction pressure is varied under the reaction conditions in which the amount of the catalyst is different from that in the reaction, the results of which are shown in FIG. 10.

Now, a production device usable in the present invention will be described in detail by way of a specific example. FIG. 1 shows an example of preferred facilities for producing a carbonate ester. FIG. 2 schematically shows the state of each of substances in each of steps performed by use of the facilities shown in FIG. 1.

(Carbonate Ester Generation Reaction)

Alcohol (1-propanol (PrOH); liquid phase), 2-cyanopyridine (2-CP; liquid phase), carbon dioxide ($CO_2$; gas phase)

supplied via a boosting pump 15, and the like are supplied from a buffer tank 1 to a reaction tube 2 filled with a solid catalyst (solid phase) containing $CeO_2$ as a main component. In the reaction tube 2 supplied with these components, the carbonate ester generation reaction is caused. New 2-cyanopyridine is used at the start of the reaction. Alternatively, 2-cyanopyridine 27 (gas phase) separated and purified in a dehydration agent separation column 6, and 2-cyanopyridine 31 (liquid phase) regenerated from 2-picolinamide purified in a water separation column 8, may be used.

In a direct synthesis device for a carbonate ester shown in FIG. 1, either one of a batch reactor, a semi-batch reactor, and a flow reactor such as a continuous tank reactor or a tube reactor may be used.

The reaction temperature (temperature of the reaction solution) in the reaction tube 2 is preferably 50 to 300° C., and more preferably 100 to 160° C. The reaction pressure in the reaction tube 2 is, for example, 0.1 to 20 MPa (absolute pressure), and preferably 0.6 to 8 MPa.

In the carbonate ester reaction tube 2, the $CeO_2$ catalyst, after being used for the generation of the carbonate ester for at least a certain time period, has the activity thereof as the catalyst decreased. When this occurs, the reaction tube 2 is supplied with washing PrOH 36 to remove the catalyst poison in order to regenerate the catalyst. Then, crude PrOH 37 containing the catalyst poison as a result of washing the reaction tube 2 is purified in a washing PrOH distillation column 9, and PrOH 38 obtained as a result of the purification is returned to a PrOH tank 10.

The PrOH tank 10 is externally supplemented with PrOH 34 as a reaction material. The PrOH tank 10 is connected with a dehydration tank filled with a dehydration agent (neither is shown), and the PrOH transmitted into the dehydration tank from the PrOH tank 10 has moisture therein removed. The PrOH 36 purified in this manner is returned to the PrOH tank 10 and is supplied to the reaction tube 2.

It is preferred that the moisture amount in the PrOH stored in the PrOH tank 10 is measured, for example, periodically, and is controlled not to exceed the upper limit, which is the control reference for the moisture amount, for example, 0.10% by weight.

A reaction solution 17 obtained as a result of the reaction is transmitted to the buffer tank 1 from the reaction tube 2. From the buffer tank 1, a reaction solution 18, which contains dipropyl carbonate (DPrC) as the target compound generated in the reaction tube 2, is transmitted to a low boiling-point fractional distillation column 3. From a top of the low boiling-point fractional distillation column 3, $CO_2$ 19, PrOH and DPrC are recovered. The $CO_2$ 19 is transmitted to the boosting pump 15 from a $CO_2$ tank 11 together with $CO_2$ 40, which is newly added, and then is used for the carbonate ester generation reaction.

A mixture 21 recovered from the low boiling-point fractional distillation column 3, namely, the mixture 12 of 2-cyanopyridine and 2-picolinamide, is transmitted to the dehydration agent separation column 6. 2-picolinamide 28 is recovered from a bottom of the dehydration agent separation column 6, and 2-cyanopyridine 27 is recovered from a top of the dehydration agent separation column 6. The recovered 2-cyanopyridine 27 is recycled to the reaction tube 2 via a 2-CP tank 13 and the buffer tank 1.

The PrOH and DPrC 20 recovered from the top of the low boiling-point component separation column 3 are transmitted to an alcohol (PrOH) recovery column 4, and crude DPrC (crude dipropyl carbonate) 23 is recovered from a bottom of the alcohol recovery column 4. The crude DPrC 23 is transmitted to a DPrC (dipropyl carbonate) purification column 5. In the meantime, PrOH 22 is recovered from a top of the alcohol recovery column 4. The recovered PrOH is recycled to the reaction tube 2 via the PrOH tank 10.

In the DPrC purification column 5, the crude DPrC 23 is purified. DPrC 24 thus obtained is recovered as a final target compound. In the meantime, impurities and the like are discarded as a waste 25.

The 2-picolinamide (2-PA; 28) recovered from the dehydration agent separation column 6 is transferred to a nitrile regeneration reactor 7 in order to be regenerated into 2-cyanopyridine. In the nitrile regeneration reactor 7, a dehydration reaction of the 2-picolinamide is caused under the presence of a catalyst containing $Cs_2O$ and diphenylether (DPE) as a solvent, and as a result, 2-cyanopyridine (2-CP) is regenerated.

2-cyanopyridine 29 may be recovered from the water separation column 7 during the reaction, or may be distilled and recovered as it is after the reaction. The recovered 2-cyanopyridine 29 is transmitted to a water separation column 8 together with a part of the DPE as the solvent. The 2-cyanopyridine 31 purified in, and recovered from, the water separation column 8 is transmitted to the reaction tube 2 via the 2-CP tank 13 and the like and is reused to produce the carbonate ester. In the meantime, DPE 30, which is the solvent recovered from the water separation column 8, is recycled to the nitrile regeneration reactor 7.

In an embodiment of the present invention described above, the PrOH 38, which is an alcohol used to produce dipropyl carbonate (DPrC) as a carbonate ester, and the PrOH 34, which is newly supplied to the reaction system, are both dehydrated in the PrOH tank 10. Thus, dipropyl carbonate (DPrC) may be selectively obtained at a high yield.

EXAMPLES

Hereinafter, the present invention will be described in more detail by way of examples of method for producing a carbonate ester. The present invention is not limited to any of the following examples.

<Moisture Measurement Method>

The moisture amount in each of the aromatic nitrile compound and the aliphatic alcohol was measured by the Karl Fischer titration method in compliance with JIS K 0113:2005 General rules for methods of potentiometric, amperometric, coulometric, and Karl Fischer titrations.

The measurement device: Hybrid Karl Fischer moisture meter MKH-700 produced by Kyoto Electronics Manufacturing Co., Ltd. (catholyte: Aquamicron CXU (produced by Mitsubishi Chemical Corporation); anolyte: Aquamicron AKX (produced by Mitsubishi Chemical Corporation))

<Component Analysis>

The amount of dipropyl carbonate (DPrC) and the amounts of propyl pyridine-2-carboximidate (2-PIPr), propyl picolinate (2-PPr) and propyl carbamate (2-PrCM) as the by-products were quantized by gas chromatography (GC).

Measurement Method: GC-FID Method
Measurement Device: Shimadzu GC-2014 Produced by Shimadzu Corporation Example 1

First, cerium oxide (impurity concentration: 0.02% or lower) was baked at 600° C. for 3 hours in an air atmosphere to obtain a powdery solid catalyst. As 1-propanol (1-PrOH), 1-propanol produced by Wako Pure Chemical Industries, Ltd. was used.

Next, 0.242 g (1.41 mmol) of the above-described solid catalyst, 14.62 g (140.43 mmol) of 2-cyanopyridine having a water content of 0.060% by mass produced by Koei Chemical Co., Ltd. as a dehydration agent, and 50.50 g (840.27 mmol) of 1-propanol having a water content of 0.064% by mass were incorporated into an autoclave (with two slant stirring paddles; material: SUS 316; capacitance: 200 mL). After $CO_2$ substitution, the system was filled with $CO_2$, and a reaction was caused at a reaction pressure of 8 MPa, a reaction temperature of 132° C. for 3 hours (3 h) (aliphatic carbonate ester generation reaction).

Then, the autoclave was cooled down. After depressurization was performed, the reaction solution was recovered. 10.59 g (86.76 mmol) of 2-picolinamide had been deposited as a by-product in the reaction solution.

Then, the reaction solution was heated in a water bath of 55° C. to dissolve the 2-picolinamide in the solution. Then, the DPrC and the by-products (2-PIPr, 2-PPr and 2-PrCM) in the reaction solution were subjected to quantization by the above-described component analysis.

As a result, 12.60 g (86.20 mmol) of DPrC and 0.064 g (0.47 mmol) of the by-products (2-PIPr, 2-PPr and 2-PrCM) were confirmed to be generated.

Example 2

The reaction was caused and the analysis was performed in substantially the same manner as in example 1 except that 1-propanol (1-PrOH) produced by Wako Pure Chemical Industries, Ltd. was used after being kept still at a temperature of 25° C. and a humidity of 40% for 7 days to have a water content of 0.0480% by mass.

As a result, 12.64 g (86.44 mmol) of DPrC and 0.063 g (0.46 mmol) of the by-products (2-PIPr, 2-PPr and 2-PrCM) were confirmed to be generated.

Example 3

The reaction was caused and the analysis was performed in substantially the same manner as in example 1 except that 0.339 g (1.97 mmol) of the above-described catalyst, 20.47 g (196.62 mmol) of 2-cyanopyridine produced by Koei Chemical Co., Ltd. as a dehydration agent, and 70.70 g (1176.37 mmol) of 1-propanol produced by Wako Pure Chemical Industries, Ltd. (1-PrOH; having a water content of 0.0184% by mass) were used and that the reaction pressure was 4 MPa.

As a result, 17.43 g (119.20 mmol) of DPrC and 0.084 g (0.61 mmol) of the by-products (2-PIPr, 2-PPr and 2-PrCM) were confirmed to be generated.

Example 4

The reaction was caused and the analysis was performed in substantially the same manner as in example 3 except that 1-propanol (1-PrOH) produced by Wako Pure Chemical Industries, Ltd. was used after being supplied with Molecular Sieves 4A ⅛ produced by Nacalai Tesque Inc. as a water absorber to have a water content of 0.0021% by mass and that the reaction pressure was 2 MPa.

As a result, 17.41 g (119.10 mmol) of DPrC and 0.091 g (0.65 mmol) of the by-products (2-PIPr, 2-PPr and 2-PrCM) were confirmed to be generated.

Example 5

The reaction was caused and the analysis was performed in substantially the same manner as in example 4 except that the reaction pressure was 1 MPa.

As a result, 16.49 g (112.80 mmol) of DPrC and 0.108 g (0.77 mmol) of the by-products (2-PIPr, 2-PPr and 2-PrCM) were confirmed to be generated.

Comparative Example 1

The reaction was caused and the analysis was performed in substantially the same manner as in example 1 except that 1-propanol (1-PrOH) produced by Wako Pure Chemical Industries, Ltd. was used after being kept still at a temperature of 25° C. and a humidity of 40% for 30 days to have a water content of 0.1441% by mass.

As a result, 6.12 g (41.85 mmol) of DPrC and 0.049 g (0.33 mmol) of the by-products (2-PIPr, 2-PPr and 2-PrCM) were confirmed to be generated.

Comparative Examples 2 Through 4

The reactions were respectively caused in substantially the same manner as in examples 3 through 5 except that 1-PrOH having a water content of 0.1441% by mass was used. The results of comparative examples 2 through 4 were analyzed.

The results are shown in Tables 2 and 3 below.

The details of the results in the above-described examples and comparative examples are shown in Tables 1 and 2, and the points of the results are shown in Table 3.

[Table 1]

| | | EXAMPLE 1 | | | | |
|---|---|---|---|---|---|---|
| CONDITIONS | | REACTION PRESSURE: 8 MPa: REACTION TEMPERATURE: 132° C.: REACTION TIME: 3 hr | | | | |
| MATERIAL | COMPONENT | MOLECULAR AMOUNT | WEIGHT (g) | MOL (mmol) | WATER CONTENT (mass %) | |
| | CeO2 CATALYST | 172.11 | 0.242 | 1.41 | — | |
| | 2-CP | 104.11 | 14.62 | 140.43 | 0.0599 | |
| | 1-PrOH | 60.10 | 50.50 | 840.27 | 0.0640 | |
| | TOTAL | — | 65.36 | | 0.0631 | |
| REACTION RESULTS | COMPONENT | MOLECULAR AMOUNT | WEIGHT (g) | MOL (mmol) | DPrC YIELD AND RATIO OF BY-PRODUCT AMOUNT | |
| | MAIN COMPONENT | DPrC | 146.19 | 12.60 | 86.2 | DPrC YIELD BASED ON 2-CP (mol %) | 61.4 |
| | BY-PRODUCT | PrCM | 103.12 | 0.024 | 0.23 | RATIO OF BY-PRODUCT AMOUNT | 0.0055 |
| | | 2-PIPr | 164.21 | 0.010 | 0.06 | | |

|   |   |   |   |   |   |   |
|---|---|---|---|---|---|---|
|   | 2-PPr | 165.19 | 0.030 | 0.18 | WITH RESPECT TO DPrC |   |
|   | TOTAL | — | 0.064 | 0.48 | TOTAL OF BY-PRODUCTS/DPrC (mmol/mmol) |   |

EXAMPLE 2

| CONDITIONS | REACTION PRESSURE: 8 MPa; REACTION TEMPERATURE: 132° C.; REACTION TIME: 3 hr |||||
|---|---|---|---|---|---|
| MATERIAL | COMPONENT | MOLECULAR AMOUNT | WEIGHT (g) | MOL (umol) | WATER CONTENT (mass %) |
|   | CeO2 CATALYST | 172.11 | 0.242 | 1.41 | — |
|   | 2-CP | 104.11 | 14.62 | 140.43 | 0.0599 |
|   | 1-PrOH | 60.10 | 50.50 | 840.27 | 0.0480 |
|   | TOTAL | — | 65.36 |   | 0.0507 |

| REACTION RESULTS |   | COMPONENT | MOLECULAR AMOUNT | WEIGHT (g) | MOL (mmol) | DPrC YIELD AND RATIO OF BY-PRODUCT AMOUNT ||
|---|---|---|---|---|---|---|---|
|   | MAIN COMPONENT | DPrC | 146.19 | 12.64 | 86.5 | DPrC YIELD BASED ON 2-CP (mol %) | 61.6 |
|   | BY-PRODUCT | PrCM | 103.12 | 0.020 | 0.19 | RATIO OF BY-PRODUCT AMOUNT WITH RESPECT TO DPrC | 0.0053 |
|   |   | 2-PIPr | 164.21 | 0.011 | 0.07 |   |   |
|   |   | 2-PPr | 165.19 | 0.032 | 0.19 |   |   |
|   |   | TOTAL | — | 0.063 | 0.45 | TOTAL OF BY-PRODUCTS DPrC (mmol/mmol) |   |

EXAMPLE 3

| CONDITIONS | REACTION PRESSURE: 8 MPa: REACTION TEMPERATURE: 132° C.; REACTION TIME: 3 hr |||||
|---|---|---|---|---|---|
| MATERIAL | COMPONENT | MOLECULAR AMOUNT | WEIGHT (g) | MOL (mmol) | WATER CONTENT (mass %) |
|   | CeO2 CATALYST | 172.11 | 0.339 | 1.97 | — |
|   | 2-CP | 104.11 | 20.47 | 196.62 | 0.0690 |
|   | 1-PrOH | 60.10 | 70.70 | 1176.37 | 0.0184 |
|   | TOTAL | — | 91.51 |   | 0.0298 |

| REACTION RESULTS |   | COMPONENT | MOLECULAR AMOUNT | WEIGHT (g) | MOL (mmol) | DPrC YIELD AND RATIO OF BY-PRODUCT AMOUNT ||
|---|---|---|---|---|---|---|---|
|   | MAIN COMPONENT | DPrC | 146.19 | 17.43 | 119.2 | DPrC YIELD BASED ON 2-CP (mol %) | 60.6 |
|   | BY-PRODUCT | PrCM | 103.12 | 0.027 | 0.26 | RATIO OF BY-PRODUCT AMOUNT WITH RESPECT TO DPrC | 0.0051 |
|   |   | 2-PIPr | 164.21 | 0.016 | 0.10 |   |   |
|   |   | 2-PPr | 165.19 | 0.041 | 0.25 |   |   |
|   |   | TOTAL | — | 0.084 | 0.61 | TOTAL OF BY-PRODUCTS/DPrC (mmol/mmol) |   |

EXAMPLE 4

| CONDITIONS | REACTION PRESSURE: 8 MPa; REACTION TEMPERATURE: 132° C.; REACTION TIME: 3 hr |||||
|---|---|---|---|---|---|
| MATERIAL | COMPONENT | MOLECULAR AMOUNT | WEIGHT (g) | MOL (mmol) | WATER CONTENT (mass %) |
|   | CeO2 CATALYST | 172.11 | 0.339 | 1.97 | — |
|   | 2-CP | 104.11 | 20.47 | 196.62 | 0.0690 |
|   | 1-PrOH | 60.10 | 70.70 | 1176.37 | 0.0021 |
|   | TOTAL | — | 91.51 |   | 0.0171 |

| REACTION RESULTS |   | COMPONENT | MOLECULAR AMOUNT | WEIGHT (g) | MOL (mmol) | DPrC YIELD AND RATIO OF BY-PRODUCT AMOUNT ||
|---|---|---|---|---|---|---|---|
|   | MAIN COMPONENT | DPrC | 146.19 | 17.41 | 119.1 | DPrC YIELD BASED ON 2-CP (mol %) | 60.6 |
|   | BY-PRODUCT | PrCM | 103.12 | 0.028 | 0.27 | RATIO OF BY-PRODUCT AMOUNT WITH RESPECT TO DPrC | 0.0055 |
|   |   | 2-PIPr | 164.21 | 0.022 | 0.13 |   |   |
|   |   | 2-PPr | 165.19 | 0.042 | 0.25 |   |   |
|   |   | TOTAL | — | 0.92 | 0.66 | TOTAL OF BY-PRODUCTS/DPrC (mmol/mmol) |   |

EXAMPLE 5

| | | | | | | |
|---|---|---|---|---|---|---|
| CONDITIONS | | REACTION PRESSURE: 8 MPa; REACTION TEMPERATURE: 132° C.; REACTION TIME: 3 hr | | | | |

| MATERIAL | COMPONENT | MOLECULAR AMOUNT | WEIGHT (g) | MOL (mmol) | WATER CONTENT (mass %) | |
|---|---|---|---|---|---|---|
| | CeO2 CATALYST | 172.11 | 0.339 | 1.97 | — | |
| | 2-CP | 104.11 | 20.47 | 196.62 | 0.0690 | |
| | 1-PrOH | 60.10 | 70.70 | 1176.37 | 0.0021 | |
| | TOTAL | — | 91.51 | | 0.0171 | |

| REACTION RESULTS | COMPONENT | | MOLECULAR AMOUNT | WEIGHT (g) | MOL (mmol) | DPrC YIELD AND RATION OF BY-PRODUCT AMOUNT | |
|---|---|---|---|---|---|---|---|
| | MAIN COMPONENT | DPrC | 146.19 | 16.49 | 112.8 | DPrC YIELD BASED ON 2-CP (mol %) | 57.4 |
| | BY-PRODUCT | PrCM | 103.12 | 0.031 | 0.30 | RATIO OF BY-PRODUCT AMOUNT WITH RESPECT TO DPrC TOTAL OF BY-PRODUCTS/DPrC (mmol/mmol) | 0.0068 |
| | | 2-PIPr | 164.21 | 0.030 | 0.18 | | |
| | | 2-PPr | 165.19 | 0.047 | 0.28 | | |
| | | TOTAL | — | 0.108 | 0.77 | | |

The by-products confirmed to be generated are the following three compounds.
PrCM: Propyl carbamate; molecular weight: 103.12M g/mol
2-PIPr: Propyl pyridine-2-carboximidate; molecular weight: 164.21M g/mol
2-PPr: Propyl picolinate; molecular weight: 165.19M g/mol

TABLE 2

COMPARATIVE EXAMPLE 1

| | | | | | | |
|---|---|---|---|---|---|---|
| CONDITIONS | | REACTION PRESSURE: 8 MPa; REACTION TEMPERATURE: 132° C.; REACTION TIME: 3 hr | | | | |

| MATERIAL | COMPONENT | MOLECULAR AMOUNT | WEIGHT (g) | MOL (mmol) | WATER CONTENT (mass %) | |
|---|---|---|---|---|---|---|
| | CeO2 CATALYST | 172.11 | 0.242 | 1.41 | — | |
| | 2-CP | 104.11 | 14.62 | 140.43 | 0.0599 | |
| | 1-PrOH | 60.10 | 50.50 | 840.27 | 0.1441 | |
| | TOTAL | — | 65.36 | | 0.1252 | |

| REACTION RESULTS | COMPONENT | | MOLECULAR AMOUNT | WEIGHT (g) | MOL (mmol) | DPrC YIELD AND RATIO OF BY-PRODUCT AMOUNT | |
|---|---|---|---|---|---|---|---|
| | MAIN COMPONENT | DPrC | 146.19 | 6.12 | 41.9 | DPrC YIELD BASED ON 2-CP (mol %) | 29.8 |
| | BY-PRODUCT | PrCM | 103.12 | 0.008 | 0.08 | RATIO OF BY-PRODUCT AMOUNT WITH RESPECT TO DPrC TOTAL OF BY-PRODUCTS/DPrC (mmol/mmol) | 0.0078 |
| | | 2-PIPr | 164.21 | 0.015 | 0.09 | | |
| | | 2-PPr | 165.19 | 0.026 | 0.16 | | |
| | | TOTAL | — | 0.049 | 0.33 | | |

COMPARATIVE EXAMPLE 2

| | | | | | | |
|---|---|---|---|---|---|---|
| CONDITIONS | | REACTION PRESSURE: 8 MPa; REACTION TEMPERATURE: 132° C.; REACTION TIME: 3 hr | | | | |

| MATERIAL | COMPONENT | MOLECULAR AMOUNT | WEIGHT (g) | MOL (mmol) | WATER CONTENT (mass %) | |
|---|---|---|---|---|---|---|
| | CeO2 CATALYST | 172.11 | 0.339 | 1.97 | — | |
| | 2-CP | 104.11 | 20.47 | 196.62 | 0.0599 | |
| | 1-PrOH | 60.10 | 70.70 | 1176.37 | 0.1441 | |
| | TOTAL | — | 91.51 | | 0.1252 | |

| REACTION RESULTS | COMPONENT | | MOLECULAR AMOUNT | WEIGHT (g) | MOL (mmol) | DPrC YIELD AND RATIO OF BY-PRODUCT AMOINT | |
|---|---|---|---|---|---|---|---|
| | MAIN COMPONENT | DPrC | 146.19 | 847 | 57.9 | DPrC YIELD BASED ON 2-CP (mol %) | 29.5 |
| | BY-PRODUCT | PrCM | 103.12 | 0.009 | 0.09 | RATIO OF BY-PRODUCT AMOUNT WITH RESPECT TO DPrC TOTAL OF BY-PRODUCTS/DPrC (mmol/mmol) | 0.0077 |
| | | 2-PIPr | 164.21 | 0.024 | 0.15 | | |
| | | 2-PPr | 165.19 | 0.036 | 0.22 | | |
| | | TOTAL | — | 0.069 | 0.45 | | |

TABLE 2-continued

COMPARATIVE EXAMPLE 3

CONDITIONS: REACTION PRESSURE: 8 MPa: REACTION TEMPERATURE: 132° C.; REACTION TIME: 3 hr

| MATERIAL | COMPONENT | MOLECULAR AMOUNT | WEIGHT (g) | MOL (mmol) | WATER CONTENT (mass %) |
|---|---|---|---|---|---|
| | $CeO_2$ CATALYST | 172.11 | 0.339 | 1.97 | — |
| | 2-CP | 104.11 | 20.47 | 196.62 | 0.0599 |
| | 1-PrOH | 60.10 | 70.70 | 1176.37 | 0.1441 |
| | TOTAL | — | 91.51 | | 0.1252 |

| REACTION RESULTS | | COMPONENT | MOLECULAR AMOUNT | WEIGHT (g) | MOL (mmol) | DPrC YIELD AND RATIO OF BY-PRODCT AMOUNT | |
|---|---|---|---|---|---|---|---|
| MAIN COMPONENT | | DPrC | 146.19 | 8.46 | 57.8 | DPrC YIELD BASED ON 2-CP (mol %) | 29.4 |
| BY-PRODUCT | PrCM | 103.12 | 0.009 | 0.09 | RATIO OF BY-PRODUCT AMOUNT WITH RESPECT TO DPrC TOTAL OF BY-PRODUCTS/DPrC (mmol/mmol) | 0.0088 |
| | 2-PIPr | 164.21 | 0.033 | 0.20 | | |
| | 2-PPr | 165.19 | 0.036 | 0.22 | | |
| | TOTAL | — | 0.079 | 0.51 | | |

COMPARATIVE EXAMPLE 4

CONDITIONS: REACTION PRESSURE: 8 MPa: REACTION TEMPERATURE: 132° C.; REACTION TIME: 3 hr

| MATERIAL | COMPONENT | MOLECULAR AMOUNT | WEIGHT (g) | MOL (mmol) | WATER CONTENT (mass %) |
|---|---|---|---|---|---|
| | $CeO_2$ CATALYST | 172.11 | 0.339 | 1.97 | — |
| | 2-CP | 104.11 | 20.47 | 196.62 | 0.0599 |
| | 1-PrOH | 60.10 | 70.70 | 1176.37 | 0.1441 |
| | TOTAL | — | 91.51 | | 0.1252 |

| REACTION RESULTS | COMPONENT | MOLECULAR AMOUNT | WEIGHT (g) | MOL (mmol) | DPrC YIELD AND RATIO OF BY-PRODUCT AMOUNT | |
|---|---|---|---|---|---|---|
| MAIN COMPONENT REACTION RESULTS | DPrC | 146.19 | 8.01 | 54.8 | DPrC YIELD BASED ON 2-CP (mol %) | 27.9 |
| | PrCM | 105.12 | 0.010 | 0.10 | | |
| | 2-PIPr | 164.21 | 0.045 | 0.27 | RATIO OF BY-PRODUCT AMOUNT WITH RESPECT TO DPrC TOTAL OF BY-PRODUCTS/DPrC (mmol/mmol) | 0.0113 |
| | 2-PPr | 164.19 | 0.041 | 0.25 | | |
| | TOTAL | — | 0.096 | 0.62 | | |

The by-products confirmed to be generated are the following three compounds.
PrCM: Propyl carbamate; molecular weight: 103.12M g/mol
2-PIPr: Propyl pyridine-2-carboximidate; molecular weight: 164.21M g/mol
2-PPr: Propyl picolinate; molecular weight: 165.19M g/mol

TABLE 3

| | REACTION PRESSURE (MPa) | REACTION TIME (h) | WATER CONTENT of 1-PrOH (mass %) | WATER CONTENT of MATERIAL (mass %) | DPrC YIELD (BASED on 2-CP) (mol %) | BY-PRODUCTS(*)/DPrC (RATIO of BY-PRODUCTS with respect to DPrC) (mmol/mmol) |
|---|---|---|---|---|---|---|
| EXAMPLE 1 | 8 | 3 | 0.064 | 0.063 | 61.4 | 0.0055 |
| EXAMPLE 2 | 8 | 3 | 0.048 | 0.051 | 61.6 | 0.0053 |
| EXAMPLE 3 | 4 | 3 | 0.018 | 0.030 | 60.6 | 0.0051 |
| EXAMPLE 4 | 2 | 3 | 0.0021 | 0.017 | 60.6 | 0.0055 |
| EXAMPLE 5 | 1 | 3 | 0.0021 | 0.017 | 57.4 | 0.0068 |
| COMPARATIVE EXAMPLE 1 | 8 | 3 | 0.141 | 0.1252 | 29.8 | 0.0078 |
| COMPARATIVE EXAMPLE 2 | 4 | 3 | 0.1441 | 0.1252 | 29.5 | 0.0077 |
| COMPARATIVE EXAMPLE 3 | 2 | 3 | 0.1441 | 0.1252 | 29.4 | 0.0088 |
| COMPARATIVE EXAMPLE 4 | 1 | 3 | 0.1441 | 0.1252 | 27.9 | 0.0113 |

The by-products confirmed to be generated are the following three compounds.
PrCM: Propyl carbamate; molecular weight: 103.12M g/mol
2-PIPr: Propyl pyridine-2-carboximidate; molecular weight: 164.21M g/mol
2-PPr: Propyl picolinate; molecular weight: 165.19M g/mol The graphs in FIG. 3 through FIG. 12 show the results of reactions caused under the same conditions as those in example 1 except that the reaction conditions presented below the respective figures were adopted and that the water content of the alcohol (water content of PrOH) was 0.064% by weight.

Figure 13:
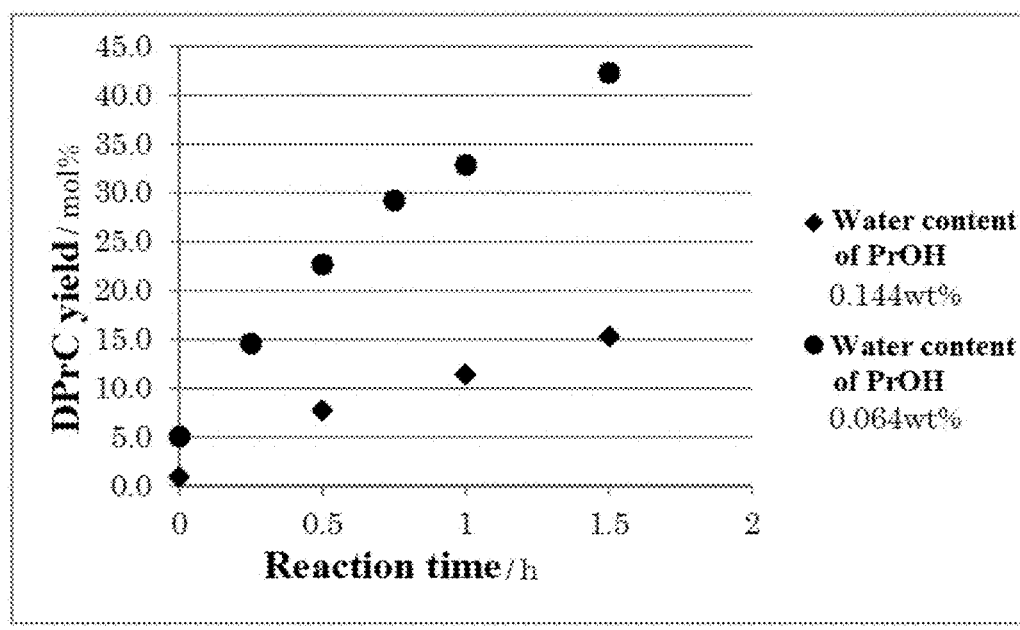
FIG. 13 is a graph showing the timewise change in the generation amount of the carbonate ester in a carbonate ester generation reaction in the case where an alcohol containing a large amount of moisture is used and in the case where an alcohol containing a small amount of moisture is used.

The graph in FIG. 13 shows the results of reactions caused under the same conditions as those in example 1 except that the reaction conditions and the water contents in the alcohol presented below FIG. 13 were adopted.

As described above, in the examples in which the moisture amount in the alcohol to be used in the carbonate ester generation reaction was suppressed, the yield of the carbonate ester was confirmed to be kept higher than in the comparative examples in which the moisture amount in the alcohol was higher. It was also confirmed that suppression of the moisture amount in the alcohol results in suppression of the generation of the by-products.

In the case where the moisture amount in the alcohol to be used for the carbonate ester generation reaction is suppressed, the effect that the activity of the catalyst in the carbonate ester generation reaction is sufficiently recovered to be reusable is recognized to be provided.

Preferred embodiments of the present invention have been described above in detail with reference to the attached drawings. The present invention is not limited to any of the embodiments. A person of ordinary skill in the art of the present invention would obviously conceive any of various altered or modified examples within the scope of technological idea defined by the claims, and such altered or modified examples are construed as being duly encompassed in the technological scope of the present invention.

REFERENCE SIGNS LIST

1 Buffer tank
2 Reaction tube
3 Low boiling-point component separation column
4 PrOH recovery column
5 DPrC purification column
6 Dehydration agent separation column
7 Nitrile regeneration reactor
8 Water separation column
9 Decompression pump
10 PrOH tank

The invention claimed is:

1. A method for producing a carbonate ester, the method comprising a carbonate ester generation reaction of reacting an alcohol and carbon dioxide with each other under the presence of an aromatic nitrile compound and a catalyst that catalyzes the carbonate ester generation reaction,
wherein the catalyst comprises $CeO_2$,
wherein a water content of the alcohol which is used for reacting with the carbon dioxide in the carbonate ester generation reaction is 0.10% by mass or less, and
wherein the method comprises controlling the water content of the alcohol which is used for reacting at 0.10% by mass water or less.

2. The method for producing a carbonate ester according to claim 1, wherein a pressure in the carbonate ester generation reaction is 0.6 MPa or higher.

3. The method for producing a carbonate ester according to claim 1, wherein a reaction temperature in the carbonate ester generation reaction is 110° C. or higher and 160° C. or lower.

4. The method for producing a carbonate ester according to claim 1, wherein a molar ratio of the aromatic nitrile compound and the alcohol is aromatic nitrile compound: alcohol=1:1 to 1:10.

5. The method for producing a carbonate ester according to claim 1, wherein a molar ratio of the catalyst, the aromatic nitrile compound and the alcohol is catalyst:aromatic nitrile compound:alcohol=1:100:200 to 0.5:100:600.

6. The method for producing a carbonate ester according to claim 1, wherein the aromatic nitrile compound comprises 2-cyanopyridine.

7. The method for producing a carbonate ester according to claim 1, wherein the alcohol comprises an aliphatic alcohol, and at least an aliphatic carbonate ester is generated as the carbonate ester.

8. The method for producing a carbonate ester according to claim 1, wherein the aliphatic alcohol is expressed by the following formula (1):

R—OH  (1)

where R is a straight or branched-chain saturated aliphatic alkyl group that may contain a substituent and has a carbon number of 1 to 10.

9. The method for producing a carbonate ester according to claim 8, wherein R in formula (1) is a saturated aliphatic alkyl group having a carbon number of 1 to 4.

10. The method for producing a carbonate ester according to claim 7, wherein the aliphatic alcohol comprises 1-propanol.

11. The method for producing a carbonate ester according to claim 1, further comprising at least one of:
dehydrating the alcohol before the alcohol is used for the carbonate ester generation reaction; and
dehydrating the alcohol after the alcohol is used for the carbonate ester generation reaction in order to reuse the alcohol.

12. The method for producing a carbonate ester according to claim 1, further comprising dehydrating, after the aromatic nitrile compound is hydrated with water generated by the carbonate ester generation reaction to generate an aromatic amide compound, the aromatic amide compound to regenerate the aromatic nitrile compound.

13. The method for producing a carbonate ester according to claim 1, wherein the controlling comprises storing the alcohol having the water content of 0.10% by mass or less.

* * * * *